(12) United States Patent
Meessen et al.

(10) Patent No.: US 9,108,164 B2
(45) Date of Patent: Aug. 18, 2015

(54) PROCESS FOR THE REMOVAL OF AMMONIA FROM AN AMMONIA-CONTAINING GAS STREAM

(71) Applicant: STAMICARBON B.V., Sittard (NL)

(72) Inventors: Jozef Hubert Meessen, Wijlre (NL); Axel Erben, Dortmund (DE); John Krijgsman, Maastricht (NL); Winfried Liebig, Iserlohn (DE)

(73) Assignees: STAMICARBON B.V., Sittard (NL); THYSSENKRUPP INDUSTRIAL SOLUTIONS AG, Essen (DE)

( * ) Notice: Subject to any disclaimer, the term of this patent is extended or adjusted under 35 U.S.C. 154(b) by 0 days.

(21) Appl. No.: 14/223,897

(22) Filed: Mar. 24, 2014

(65) Prior Publication Data

US 2014/0284214 A1   Sep. 25, 2014

Related U.S. Application Data

(63) Continuation of application No. 11/792,285, filed as application No. PCT/EP2005/012199 on Nov. 11, 2005, now Pat. No. 8,808,517.

(30) Foreign Application Priority Data

| Dec. 8, 2004 | (EP) | ................................ 04078338 |
| Feb. 28, 2005 | (EP) | ................................ 05075478 |

(51) Int. Cl.

| *B01D 61/46* | (2006.01) |
| *B01D 61/42* | (2006.01) |
| *B01D 53/58* | (2006.01) |
| *B01D 53/73* | (2006.01) |
| *B01D 61/44* | (2006.01) |
| *C07C 273/14* | (2006.01) |
| *C02F 1/469* | (2006.01) |
| *C02F 101/16* | (2006.01) |
| *C02F 103/18* | (2006.01) |

(52) U.S. Cl.
CPC .............. *B01D 61/422* (2013.01); *B01D 53/58* (2013.01); *B01D 53/73* (2013.01); *B01D 61/44* (2013.01); *B01D 61/445* (2013.01); *C07C 273/14* (2013.01); *C02F 1/4693* (2013.01); *C02F 2101/16* (2013.01); *C02F 2103/18* (2013.01)

(58) Field of Classification Search
USPC ......................................................... 204/630
See application file for complete search history.

(56) References Cited

U.S. PATENT DOCUMENTS

| 4,424,072 A | 1/1984 | Lerner |
| 4,449,900 A | 5/1984 | Lerner |
| 6,632,967 B2 | 10/2003 | Scholten et al. |

FOREIGN PATENT DOCUMENTS

| EP | 0 099 176 A | 1/1984 |
| GB | 790 510 | 2/1958 |
| GB | 2 383 034 A | 6/2003 |

OTHER PUBLICATIONS

International Search Report mailed Apr. 5, 2006 in PCT/EP2005/012199.

(Continued)

*Primary Examiner* — Arun S Phasge
(74) *Attorney, Agent, or Firm* — Nixon & Vanderhye P.C.

(57) ABSTRACT

The invention is directed to a process for the removal of ammonia from an ammonia-containing gas stream by treating the ammonia in the ammonia-containing gas stream with an acid, during which treatment an aqueous stream comprising an ammonium salt, wherein the aqueous stream comprising the ammonium salt is treated with electrodialysis, whereby the acid is recovered and an aqeos stream comprising an ammonium hydroxide salt is formed.

1 Claim, 2 Drawing Sheets

(56) References Cited

OTHER PUBLICATIONS

Written Opinion mailed Apr. 5, 2006 in PCT/EP2005/012199.
First Examination Report, Appln. No. 4139/DELNP/2007, Nov. 21, 2012.
Fertilizer Manual, The Netherlands, 1998, pp. 259-260.
Booklet No. 5 of 8: Production of Urea and Urea Ammonium Nitrate, European Fertilizer Manufacturers' Association, 1995, pp. 1-39.
Ali et al, Coupling of bipolar membrane electrodialysis and ammonia stripping for direct treatment of wastewaters containing ammonium nitrate, 2004, Journal of Membrane Science 244, pp. 89-96.

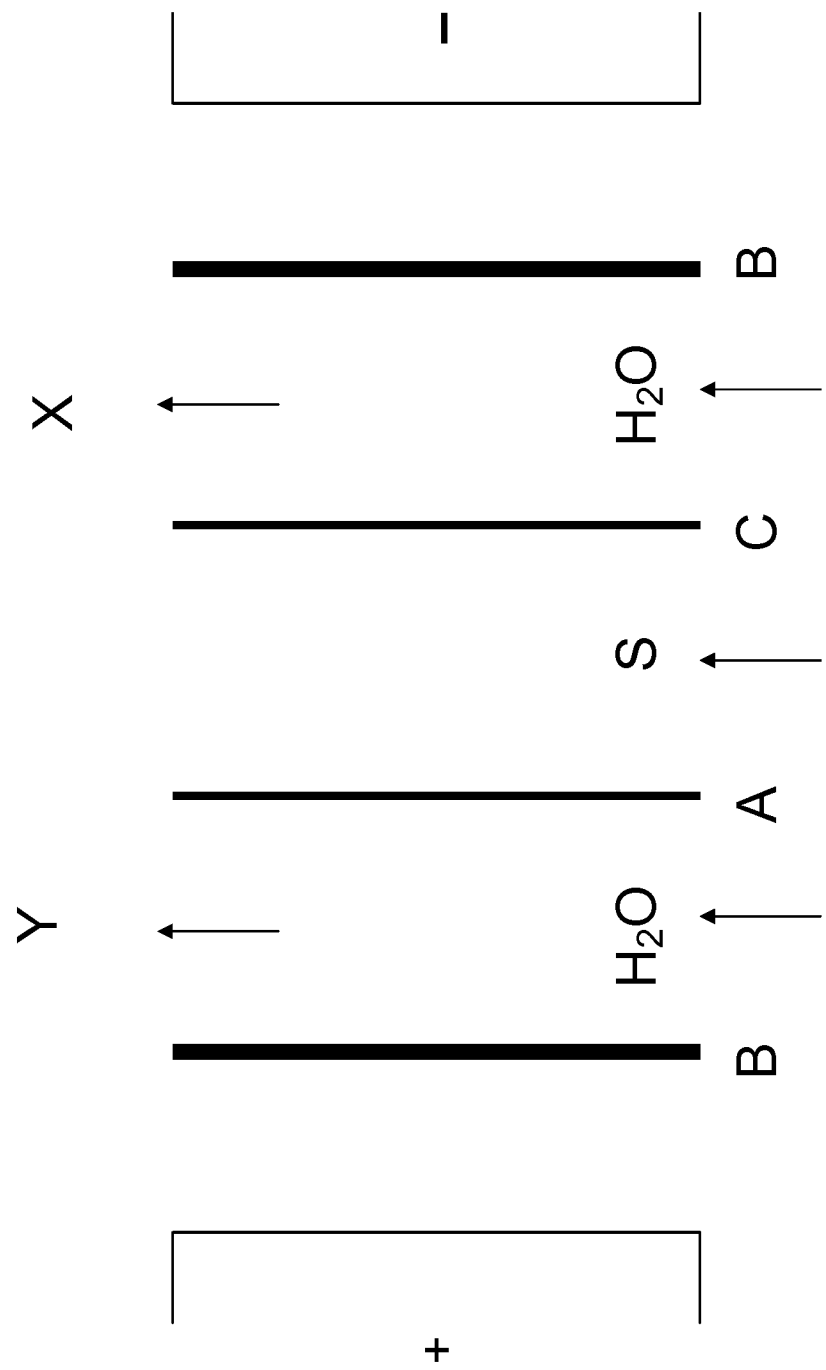

PROCESS FOR THE REMOVAL OF AMMONIA FROM AN AMMONIA-CONTAINING GAS STREAM

CROSS-REFERENCE TO RELATED APPLICATIONS

This application is a continuation of commonly owned U.S. application Ser. No. 11/792,285 filed Jul. 11, 2007 (now U.S. Pat. No. 8,808,517), which in turn is the national phase application under 35 USC §371 of PCT/EP2005/012199, filed Nov. 11, 2005, which designated the U.S. and claims priority to EP Application No. 04078338.3, filed Dec. 8, 2004 and EP Application No. 05075478.7, filed Feb. 28, 2005, the entire contents of each of which are hereby incorporated by reference.

FIELD

The invention is directed to a process for the removal of ammonia from an ammonia-containing gas stream by treating the ammonia in the ammonia-containing gas stream with an acid, during which treatment an aqueous stream comprising an ammonium salt is formed.

BACKGROUND AND SUMMARY

Ammonia has to be removed from gas streams that are vented into the air, because it causes environmental problems. Governmental regulations with respect to ammonia emissions will become stricter in future.

A process for the removal of ammonia from an ammonia containing gas stream is described, for instance, in U.S. Pat. No. 4,424,072.
In this patent specification is described that the ammonia is removed from the gas stream exiting from the top of a prilling tower in a urea plant by contacting the gas stream in a scrubber with a non-volatile, dilute acid solution whereby the $NH_3$ is absorbed. According to U.S. Pat. No. 4,424,072, non-volatile acid solutions include inorganic acids such as phosphoric acid, sulphuric acid and nitric acid as well as organic acids such as citric acid, oxalic acid and comparable non-volatile organic acids. According to U.S. Pat. No. 4,424,072 the ammonia-free gas stream is vented to the air. It is mentioned that the obtained aqueous stream comprising the ammonium salt leaving the scrubbing section in the prilling tower can be recycled to the urea production process.

The drawback of using the process according to U.S. Pat. No. 4,424,072, wherein the aqueous stream comprising the ammonium salt is recycled to the urea production process, is that contaminations by ammonium salts may occur in the final product, in this case urea, which contaminations are undesirable. For instance, ammonium salts in urea will usually render this urea unsuitable for the preparation of melamine. The separate processing of these ammonium salts (e.g. as a by-product) costs money and energy or often poses an environmental problem.

It has been found that the aforementioned drawback can be eliminated with a process wherein the aqueous stream comprising the ammonium salt is treated with electrodialysis, whereby the acid is recovered and an aqueous stream comprising an ammonium hydroxide salt is formed.

By performing the electrodialysis on the aqueous stream comprising the ammonium salt the acid that has been used to remove the ammonia can be recovered and an aqueous stream comprising the ammonium salt is not recycled to the urea production causing contamination of the produced urea.

BRIEF DESCRIPTION OF THE DRAWINGS

FIG. 2 is a schematic diagram of an arrangement of an electrochemical cell composed of an anion-permeable membrane (A), a cation-permeable membrane (C) and bipolar membranes (B) that may be employed as the electrodialysis apparatus in the electrodialysis section shown in FIG. 1.

DETAILED DESCRIPTION

Figure 1:
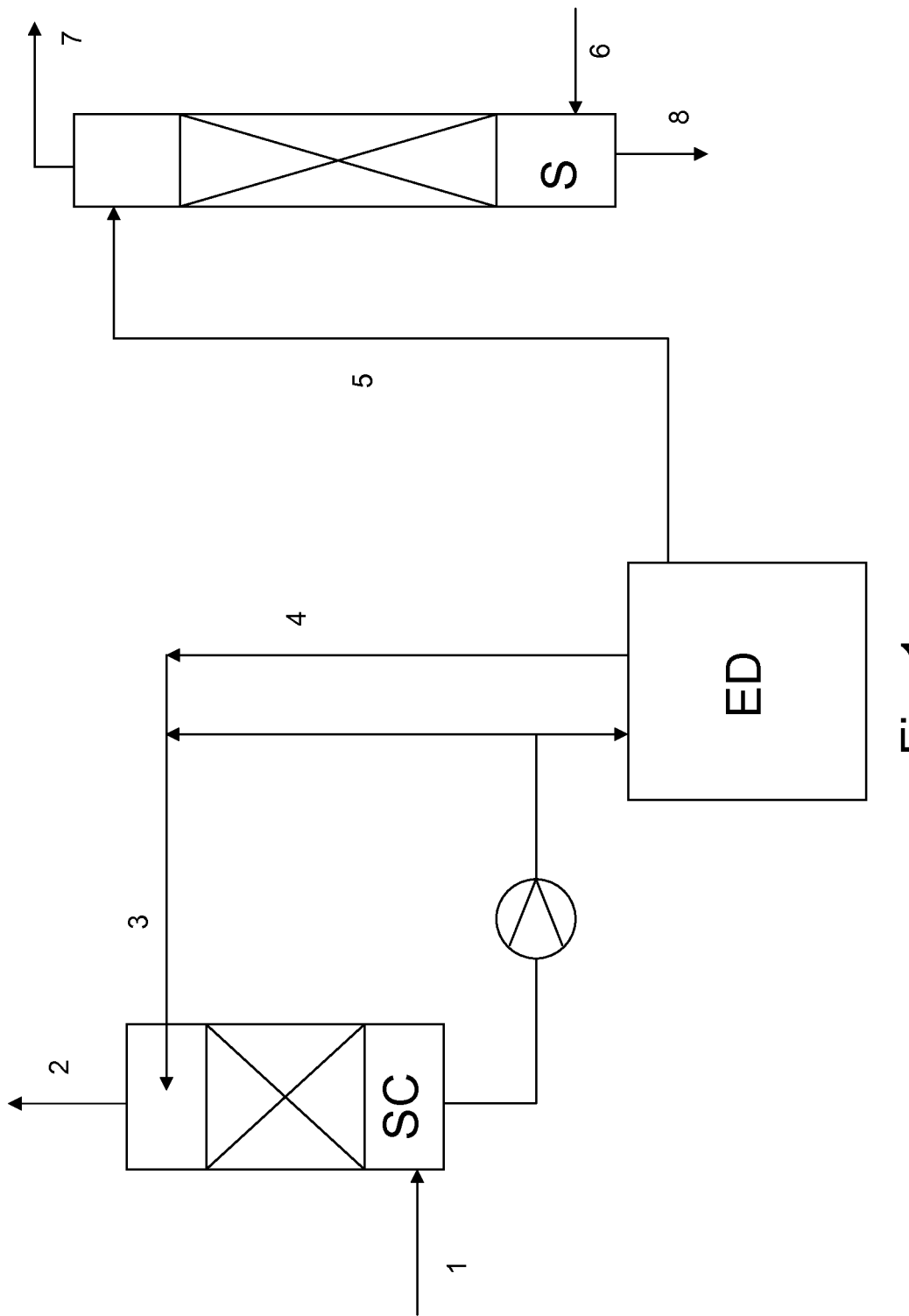
FIG. 1 is a schematic diagram showing an electrodialysis section according to an embodiment of the invention.

According to the process for the removal of ammonia from an ammonia-containing gas stream according to the invention the aqueous stream comprising the ammonium salt is treated with electrodialysis.

Here and hereafter electrodialysis is defined as an electrolytical process comprising an anode and a cathode which also comprises at least one membrane situated between the anode and cathode. This membrane can be an anion-permeable membrane, a cation-permeable membrane or a combination of one or more of these membranes with at least two bipolar membranes. Anion-permeable membranes and cation-permeable membranes are permeable for anions respectively cations when these ions are attracted by the cathode respectively the anode. Bipolar membranes consist of an anion-permeable membrane and a cation-permeable membrane laminated together. When this bipolar membrane is oriented such that the cation-permeable membrane faces the cathode water is split into protons and hydroxyl ions.

During the treatment of the aqueous stream comprising the ammonium salt the acid used for converting the ammonia in the ammonia-containing gas stream is recovered. This acid can thus be reused for converting the ammonia in the ammonia-containing gas stream. Acids that can be used for converting the ammonia are, for example, the organic acids and inorganic acids mentioned in U.S. Pat. No. 4,424,072, as described above.

During the process according to the invention also an aqueous stream containing ammonium hydroxide is formed during the electrodialysis of the aqueous stream comprising the ammonium salt. After its formation this aqueous stream containing ammonium hydroxide can be heat treated, whereby a gaseous ammonia stream is formed.

The ammonia-containing gas stream can originate from various chemical processes, like the ammonia, urea and melamine production processes, but also from agricultural sources. The process according to the invention is in particular suitable for the treatment of ammonia-containing gas streams that contain low amounts of ammonia. These ammonia-containing gas streams are difficult to treat in an other way, for instance by separation and condensation, for removal of ammonia from these gas streams. Examples of ammonia-containing gas streams containing low amounts of ammonia are the gas streams that leave the prilling or the granulation sections of urea plants.

When the ammonia-containing gas stream, to be treated by the process according to the invention, is originating from the ammonia, urea or the melamine production processes the gaseous ammonia stream can be recycled to these processes. Before recycling the gaseous ammonia stream the gaseous stream can be treated to concentrate the ammonia in the gaseous stream.

Electrodialysis is performed in an electrochemical cell comprising an anode and cathode separated by an anion-permeable membrane or a cation-permeable membrane. Also a combination of one or more of these membranes with at least two bipolar membranes can be used. For the conversion of the ammonium salt in the aqueous stream in such a way that an acid is recovered and an ammonium hydroxide salt is formed, preferably the anode and the cathode are separated by at least one anion-permeable membrane. More preferably the electrochemical cell also comprises bipolar membranes and a cation-permeable membrane.

The invention is also directed to an electrodialysis section for treatment of an ammonia-containing gas stream comprising
- a scrubber, wherein an ammonia-containing gas stream is contacted with an acid,
- an electrodialysis apparatus, wherein a stream comprising an acid and a stream comprising an ammonium hydroxide salt are generated.

Preferably, the electrodialysis section also comprises a stripper wherein the stream comprising an ammonium hydroxide salt is heated and a gaseous ammonia stream is formed.

The electrodialysis section preferably is incorporated into a urea plant, comprising a prilling section or a granulation section, to treat the ammonia-containing gas stream leaving the prilling or granulation section.

The invention will be further explained in detail with reference to the accompanying FIGS. 1 and 2. In FIG. 1 an electrodialysis section according to the invention is shown.

It comprises a scrubber (SC) wherein an ammonia-containing gas stream (1) is contacted with an acid solution (3). Clean air is vented from the scrubber via (2). The acid solution containing also the captured ammonia as an ammonium salt is transported with a pump partly to the electrodialysis apparatus (ED) and partly back to the scrubber. The electrodialysis apparatus comprises at least one membrane located between an anode and a cathode. A stream comprising the acid (4) is generated in the electrodialysis apparatus (ED) and recycled to the scrubber (SC) and an other stream comprising an ammonium hydroxide salt (5), also generated in the electrodialysis apparatus, is fed to the stripper (ST). In the stripper (ST) the ammonium hydroxide is converted with the aid of steam (6) in a gaseous ammonia stream (7), comprising water.

Two examples of possible configurations of an electrodialysis apparatus according to the invention will be explained in more detail.

According to the first configuration the electrodialysis apparatus consists of electrochemical cells comprising one anion-permeable membrane situated between an anode and a cathode dividing the cell in an anode compartment and a cathode compartment. To the cathode compartment the solution comprising the ammonium salt is fed. In the electrodialysis apparatus the acid is formed in the anode compartment and the ammonium hydroxide salt is formed in the cathode compartment. A sulfuric acid solution with a pH between 0 and 2 can be used as the acid. In the scrubber ammoniumsulphate is formed. A part of the solution leaving the scrubber and containing the ammoniumsulphate is fed to the cathode compartment of the electrochemical cell. The sulphate ions are transferred through the membrane and are thereafter, in the anode compartment, converted into sulfuric acid. The ammonium ions are, in the cathode compartment, converted into ammonium hydroxide. Part of the sulfuric acid solution is recycled to the scrubber and part of the ammonium hydroxide solution is treated in the stripper.

According to the second configuration the electrodialysis apparatus consists of electrochemical cells comprising an anion permeable membrane and/or a cation permeable membrane and bipolar membranes situated between an anode and a cathode and ordered in a way known to a person skilled in the art. The electrochemical cell can for instance be a so-called three-compartment cell according to FIG. 2.

The ammonia-containing gas stream was contacted with a nitric acid solution with a pH between 0 and 2 in the scrubber. A part of the resulting solution comprising ammoniumnitrate is fed to the electrochemical cells in the electrodialysis apparatus. The electrochemical cell is composed of an anion-permeable membrane (A), a cation-permeable membrane (C) and bipolar membranes (B) in an arrangement according to FIG. 2. The solution comprising ammoniumnitrate (S) was fed to the electrochemical cell. Water was split within the bipolar membrane and a nitric acid solution (Y) and ammonium hydroxide solution (X) are formed. Part of the nitric acid solution is recycled to the scrubber and part of the ammonium hydroxide solution is treated in the stripper.

The invention claimed is:
1. A urea plant comprising:
a prilling section or a granulation section which generates an ammonia-containing gas stream, and
an electrodialysis section which receives and treats the ammonia-containing gas stream leaving the prilling or granulation section, wherein the electrodialysis section comprises:
(i) a scrubber in which the ammonia-containing gas stream is contacted with an acid to form an aqueous stream comprising an ammonium salt,
(ii) an electrodialysis apparatus for receiving the aqueous stream comprising an ammonium salt from the scrubber and generating a stream comprising an acid and an aqueous stream consisting of ammonium hydroxide,
(iii) a stripper for heating the aqueous stream consisting of ammonium hydroxide and forming a gaseous ammonia stream, and
(iv) a recirculation line for recirculating the gaseous ammonia stream formed in the stripper within the urea plant.

* * * * *